United States Patent [19]
Hamblen

[11] Patent Number: 5,454,719
[45] Date of Patent: Oct. 3, 1995

[54] STERILE DENTAL PACKS AND METHOD OF UTILIZING SAME

[76] Inventor: Lamae E. Hamblen, 4908 Grover St., Omaha, Nebr. 68106

[21] Appl. No.: 262,162

[22] Filed: Jun. 20, 1994

Related U.S. Application Data

[63] Continuation-in-part of Ser. No. 72,830, Jun. 7, 1993, abandoned, which is a continuation-in-part of Ser. No. 923,665, Aug. 3, 1992, abandoned.

[51] Int. Cl.⁶ ................................ A61C 5/00; A61C 5/14
[52] U.S. Cl. .............................................. 433/215; 433/136
[58] Field of Search ...................................... 433/136, 137, 433/138, 215; 602/41, 43, 44, 45, 53

[56] References Cited

U.S. PATENT DOCUMENTS

| | | |
|---|---|---|
| 525,797 | 9/1894 | Richmond ................................ 433/136 |
| 1,245,153 | 11/1917 | Evslia . |
| 1,438,064 | 12/1922 | Simmons . |
| 1,997,467 | 4/1935 | Manley ................................ 32/33 |
| 3,705,585 | 12/1972 | Saffro ................................ 128/303.1 |
| 4,372,314 | 2/1983 | Wall ................................ 128/296 |
| 4,685,883 | 8/1987 | Jernberg ................................ 433/215 |
| 4,813,872 | 3/1989 | Knitter ................................ 433/136 |
| 5,000,746 | 3/1991 | Meiss ................................ 604/304 |

Primary Examiner—Nicholas D. Lucchesi
Attorney, Agent, or Firm—Henderson & Sturm

[57] ABSTRACT

Sterile gauze dental packs for placement within a tooth extraction site socket to control bleeding by direct pressure. The packs are of various sizes and shapes so as to conform to differing extraction sockets for both adults and children. The sterile gauze prevents infection and the different configurations increase comfort, provides hemostasis by direct pressure, reduce infection risks, and minimize material waste.

3 Claims, 2 Drawing Sheets ing 5,454,719

STERILE DENTAL PACKS AND METHOD OF UTILIZING SAME

CROSS REFERENCE TO RELATED APPLICATION

The present application is a continuation-in-part of U.S. patent application Ser. No. 08/072,830 filed Jun. 7, 1993, which in turn is a continuation-in-part of Ser. No. 07/923,665 filed on Aug. 3, 1992, both now abandoned.

TECHNICAL FIELD

The present invention relates to the field of dental packs for tooth extraction sites, and in particular to sterile dental packs having a size and shape designed to conform to the extraction site socket of single and multiple tooth extractions.

BACKGROUND ART

As can be seen by reference to the following U.S. Pat. Nos. 1,095,264; 2,501,544; 2,396,203; 3,705,585 and 4,372,314; the prior art is replete with myriad and diverse surgical dressing packs used to stem the bleeding precipitated by a dental extraction.

While all of the aforementioned prior art constructions are adequate for the basic purpose and function for which they have been specifically designed, these patented devices, as well as the cylindrical cotton packs and rolled or folded gauze pads in common usage, are generally deficient in a variety of ways. To begin with, neither the cylindrical packs nor the rolled pads or folded pads are maintained in a sterile condition and they employ far more material than is necessary which can cause discomfort for the patient. Furthermore, they are not effective for hemostasis as they do not conform to the extraction socket but rather merely cover the extraction site in an attempt to stem the flow of blood until a clot can form within the extraction socket. As to the patented packs, these constructions are generally too complex and costly to be employed on a large scale basis by most practicing dentists.

As a consequence of the foregoing situation, there has existed a longstanding need among dentists and dental technicians for a simple, inexpensive, sterile dental pack that will produce the desired hemostasis with the minimum amount of material in a shape that readily conforms to the socket created by the extraction of a tooth.

DISCLOSURE OF THE INVENTION

Briefly stated, the sterile dental packs that form the basis of the present invention comprise sterilized, compacted spherical and oblong packs fabricated from gauze in a variety of sizes and that will readily conform to the different sized orifices or sockets that are created by dental extractions. As will be explained in greater detail further on in the specification, the dental pack construction of this invention represents a significant advance over the prior art packing in that the size and shape of this new packing will place the new packing in direct contact with a larger exposed area of capillary bleeding within the dental extraction site, thereby increasing the effectiveness of direct pressure that can be applied to the packing to control bleeding.

In addition, the new packing will be sterile and intended to be handled only by the patient, thereby limiting the possibility that an infection or disease will be transmitted either from or through the open bleeding area at the extraction site.

BRIEF DESCRIPTION OF THE DRAWINGS

These and other attributes of the invention will become more clear upon a thorough study of the following description of the best mode for carrying out the invention, particularly when reviewed in conjunction with the drawings, wherein.

BEST MODE FOR CARRYING OUT THE INVENTION

Figure 1:
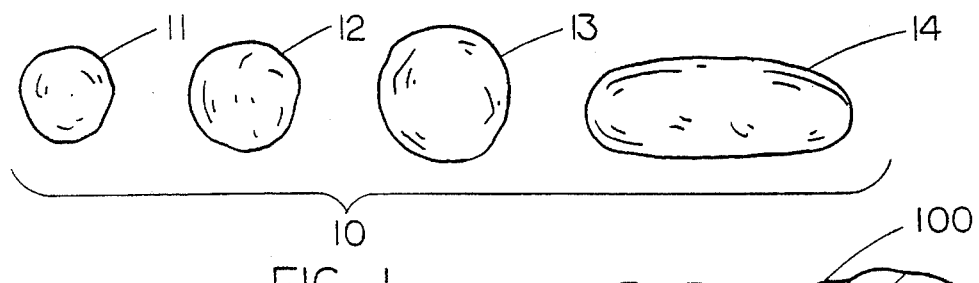
FIG. 1 is an perspective view of a variety of differently sized and shaped dental packs fabricated in accordance with the teachings of this invention.

As can be seen by reference to the drawings, and in particular to FIG. 1, the spherical and oblong dental packs that form the basis of the present invention are designated generally by the reference number (10). The dental packs (10) are fabricated from gauze formed and sewn into compacted three dimensional shapes preferably having a spherical cross-section (11, 12, 13, and 14) and having different diameters and lengths to accommodate different sized sockets created by extractions performed on both children's and adult's teeth. After fabrication, the dental packs (11, 12, 13, and 14) are sterilized in a manner well known in the art.

Figure 2:
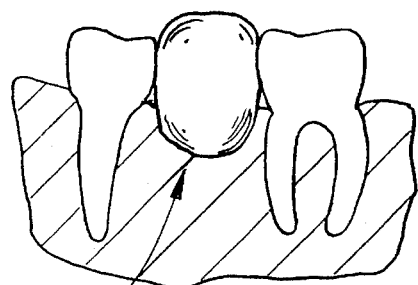
FIG. 2 is a cross-sectional view of a spherical packing situated in an extraction site socket.
Figure 3:
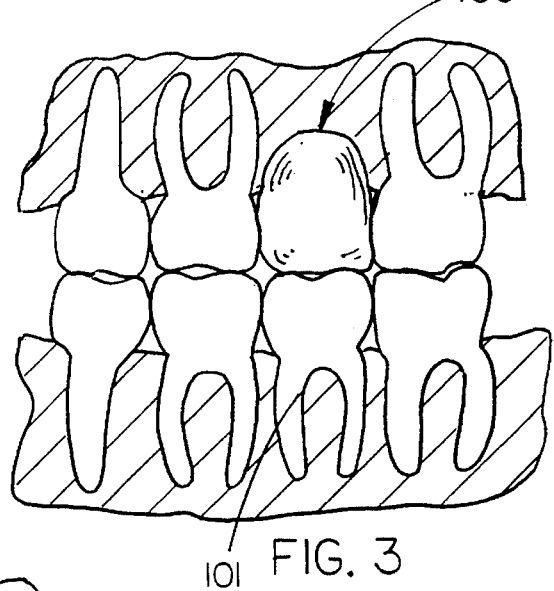
FIG. 3 is a cross-sectional view of the spherical pack being compressed between the patient's teeth to provide direct pressure within the extraction socket.
Figure 8:
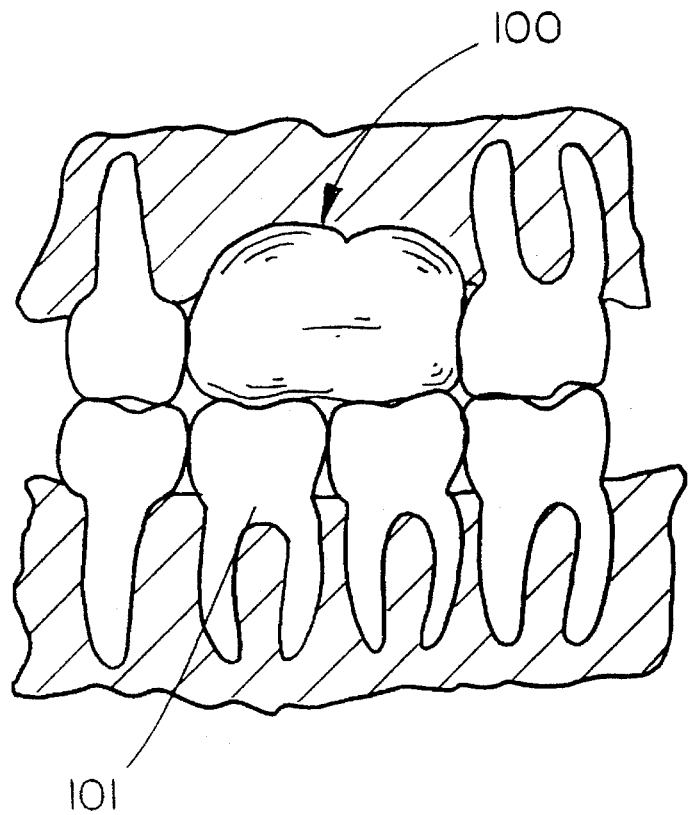
FIG. 8 is a side elevation view of an oblong embodiment of the present invention situated in a double extraction socket.

As shown in FIGS. 2, 3, and 8, the spherical and oblong dental packs (10) are configured to be inserted within the socket (100) created by the tooth extraction so that direct pressure may be applied to the bleeding tissue. A portion of the pack (10) extends from the socket (100) between the remaining teeth and is held in place by the opposing teeth (101). Given the compacted nature of the dental packing (10), virtually all of the compressive force applied by the opposing teeth (101) facing the extraction site (100) is transmitted through substantially all of the mass of the spherical dental packing, resulting in much more effective hemostasis.

Figure 4:
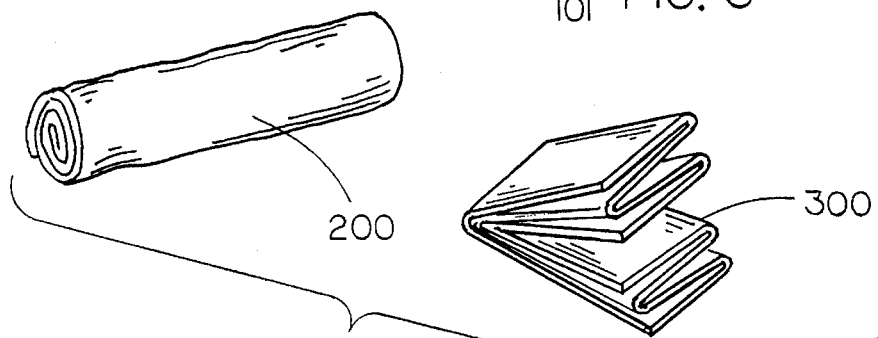
FIG. 4 is a perspective view of the prior art conventional packing.
Figure 5:
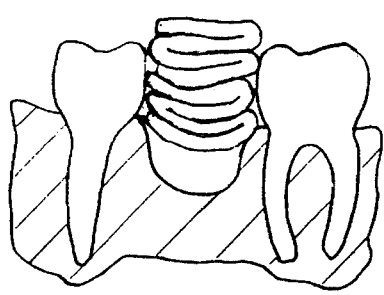
FIG. 5 is a cross-sectional view of the prior art packing placed over the extraction site socket.
Figure 6:
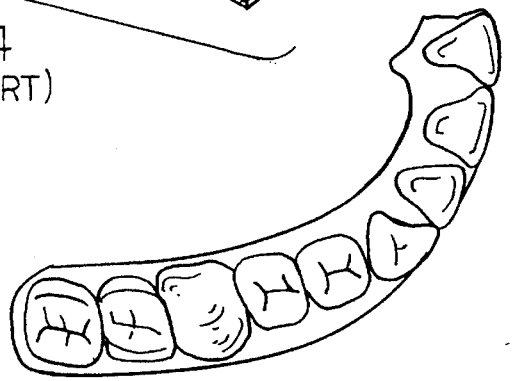
FIG. 6 is a top plan view of the minimal space occupied by the dental packing of this invention.
Figure 7:
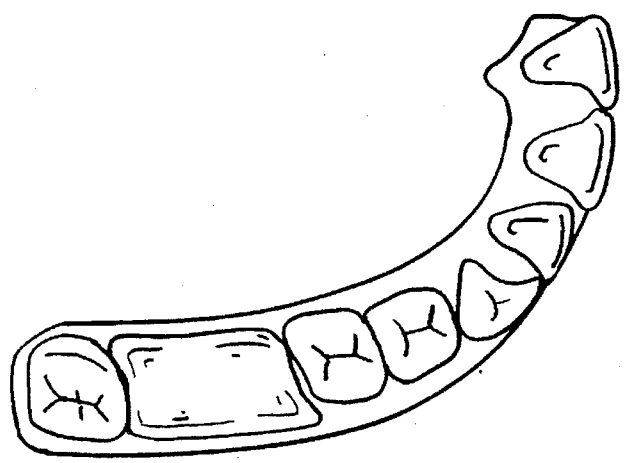
FIG. 7 is a top plan view of an oblong embodiment of the present invention situated in a double extraction socket.

By comparison, the conventional prior art dental packing depicted in FIGS. 4 and 5 comprise either an elongated cylinder (200) of cotton or a folded gauze pad (300). These packs are then placed over the extraction socket as opposed to within the socket. Therefore there is no direct pressure on the bleeding tissue and the pack merely functions to soak up blood while, hopefully, a clot forms within the socket.

As a consequence of these significant configurational and functional differences between the prior art constructions (200) and (300), as compared to the dental packs (10) of this invention, it can be seen that the vast majority of the mass of the conventional constructions serves no useful purpose. Putting it another way, it should be appreciated that the total mass of only one of the conventional packing constructions could be used to produce a number of the new dental packs.

Furthermore, since the dental packs (10) of this invention are produced in a variety of sizes (11, 12, 13, and 14), material waste is further minimized by the judicious selection of the particular size to be employed in a given extraction site socket (100).

As was mentioned previously, the dental packs (10) are fabricated from gauze and are then sterilized and are intended to be stored in hermetically sealed packaging (not shown) prior to use to maintain their sterile condition.

DESCRIPTION OF EXEMPLARY CONSTRUCTION AND USE

I. Exemplary Description:
  Extraction Gauze Dental Packs are sterile, oblong or spherical shaped, moderately compacted balls of gauze in graduated sizes to conform with the size of a dental extraction site socket.

II. Exemplary Dimensions:
  A. Spherical shaped gauze 0.25 inch in diameter for use with children (11).
  B. Spherical shaped gauze 0.5 inch in diameter for use with a moderately sized orifice (12).
  C. Spherical shaped gauze 0.75 inch in diameter for larger dental extraction sites (13).
  D. Oblong shaped gauze dental pack 0.5 inch in diameter and 1.25 inches long for use where two or more teeth in the same locus have been extracted (14).

III. Exemplary Packaging:
  Six gauze packs of the same size may be sterilized and packaged in sealed small paper bags. These may be provided to the patient by the dentist to take home following dental extractions.

IV. Comparison of features of the new Extraction Gauze Dental Packs versus standard unsterile gauze 2×2's (200) (FIGS. 4 & 5):
  A. Hemostasis
    1. The present invention provides dental packs with a size and shape which allows them to more effectively contact the capillary wound bleeding area. This results in increased pressure to the site and gives better bleeding control.
    2. Standard 2×2 gauze packs do not give effective bleeding control as it is impossible to fold (300, FIG. 4) them to conform to the bleeding area within the socket. The bleeding areas therefore do not receive effective pressure which is needed to control bleeding.
  B. Pain and Comfort:
    1. The spherical and oblong shape of the packs fit in the orifice and are less bulky in the mouth. Less discomfort is noted at the site.
    2. The 2×2's do not fold to conform to the shape of the mouth and are uncomfortable. It is also difficult for users to speak or close their mouth (FIG. 5).
  C. Convenience:
    1. The present invention may be manufactured in various sizes for child or adult use (FIG. 1). The dental packs may be provided in a package of six (not shown) in a size suitable for controlling the bleeding of each extraction site. Such packages are compact and may easily be provided to patients.
    2. The 2×2's are usually placed in an unsealed writing envelope and sent home with the patient.
  D. Infection Control
    1. The present dental packs are sterilized and are handled only by the patient.
    2. The 2×2's (FIG. 4) are not sterile and are usually sent home in a paper envelope.
    3. With the increased fear of AIDS and the increased precautions that are taken by the dentists, it is dangerous to utilize unsterile gauze packs on open bleeding areas.
    Additionally, the 2×2's (FIG. 4) are commonly touched by the dentist with unsterile hands and gloves before they are provided to a patient. The mouth is not sterile but the packs of the present invention would be an added precaution to control a possible bacterial infection or the spread of disease.

In addition, since only the patient is intended to come into contact with the sterile gauze, the likelihood of infections being passed between either the dentist or oral surgeon and the patient, or vice-versa, is significantly reduced.

Having thereby described the subject matter of the present invention, it should be apparent that many substitutions, modifications and variations of the present invention are possible in light of the above teachings. It is therefore to be understood that the invention as taught and described herein is only to be limited to the extent of the breadth and scope of the appended claims.

I claim:

1. A process for promoting healing and controlling bleeding in dental extraction sites comprising the steps of:
  (a) providing sterile cotton gauze dental packs having sizes and shapes generally conforming to the sizes and shapes of dental extraction sockets of a patient;
  (b) inserting said dental packs to within said dental extraction sockets of said patient such that said packs conform to the extraction sockets; and
  (c) providing sufficient force to said dental packs to accomplish hemostasis by direct pressure within said extraction sockets.

2. The process of claim 1 wherein said dental packs are generally spherical in configuration and have differing diameters to accommodate different sized extraction sockets.

3. The process of claim 1 wherein said dental packs are oblong and have differing diameters and lengths to accommodate multiple extraction sockets.

* * * * *